(12) United States Patent
Reddy et al.

(10) Patent No.: US 8,134,008 B2
(45) Date of Patent: *Mar. 13, 2012

(54) PREPARATION OF AMORPHOUS HYDROUS ESOMEPRAZOLE MAGNESIUM

(75) Inventors: Manne Satyanarayana Reddy, Hyderabad (IN); Muppa Kishore Kumar, Hyderabad (IN); Koilkonda Purandhar, Hyderabad (IN); Keshaboina Sreenath, Hyderabad (IN)

(73) Assignees: Dr. Reddy's Laboratories Limited, Hyderabad, Andhra Pradesh (IN); Dr. Reddy's Laboratories, Inc., Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/568,301

(22) Filed: Sep. 28, 2009

(65) Prior Publication Data

US 2010/0016606 A1  Jan. 21, 2010

Related U.S. Application Data

(62) Division of application No. 10/651,306, filed on Aug. 28, 2003, now Pat. No. 7,612,098.

(30) Foreign Application Priority Data

Aug. 30, 2002 (IN) ............................ 638/MAS/2002

(51) Int. Cl.
*C07D 401/12* (2006.01)
(52) U.S. Cl. .................................................. 546/273.7
(58) Field of Classification Search ................ 546/273.7
See application file for complete search history.

(56) References Cited

U.S. PATENT DOCUMENTS

| 6,162,816 | A | 12/2000 | Bohlin et al. |
| 6,369,085 | B1 | 4/2002 | Cotton et al. |
| 6,713,495 | B1 | 3/2004 | Sherman |
| 6,894,066 | B2 | 5/2005 | Sherman |
| 7,612,098 | B2 * | 11/2009 | Reddy et al. .............. 514/338 |
| 2003/0212274 | A1 | 11/2003 | Vijayaraghavan et al. |

FOREIGN PATENT DOCUMENTS

| EP | 0124495 A2 | 11/1984 |
| WO | 98/54171 A1 | 12/1998 |
| WO | 00/30612 A1 | 6/2000 |
| WO | 01/36409 A1 | 5/2001 |
| WO | 01/87831 A2 | 11/2001 |

OTHER PUBLICATIONS

Muzaffar, et al., "Polymorphism and Drug Availability," J. of Pharmacy (Lahore), 1979, 1(1), 59-66.
Doelker, "Physicochemical Behavior of Active, etc.," CA 132:325872 (1999).
Brittain et al., Polymorphism in Pharmaceutical Solids, NY: Marcel Dekker, Inc., 1999, pp. 1-2, 183,226.
Jain et al., "Polymorphism in Pharmacy," Indian Drugs, 1986, 23 (6), pp. 315-329.
Ulicky et al., "Comprehensive Dictionary of Physical Chemistry," NY: PTR Prentice Hall, 1992, p. 21.
Threifall, "Analysis of Organic, etc.," Analyst, 1995, vol. 120, pp. 2435-2460.
Doelker, S.T.P. Pharma Pratiques (1999), 9(5), 399-409, English translation, pp. 1-33.
Nururkar, et al., "Properties of Solids That Affect Transport," Transport Processes in Pharmaceutical Systems, NY: Marcel Dekker, Inc., 2000 pp. 575-611.

* cited by examiner

*Primary Examiner* — Patricia Morris
(74) *Attorney, Agent, or Firm* — Thomas C. McKenzie; Robert A. Franks

(57) ABSTRACT

A hydrate of esomeprazole magnesium in the form of an amorphous solid is provided. Methods of preparation and use of, as well as formulation containing the hydrate of esomeprazole magnesium in the form of an amorphous solid are also provided.

5 Claims, 3 Drawing Sheets

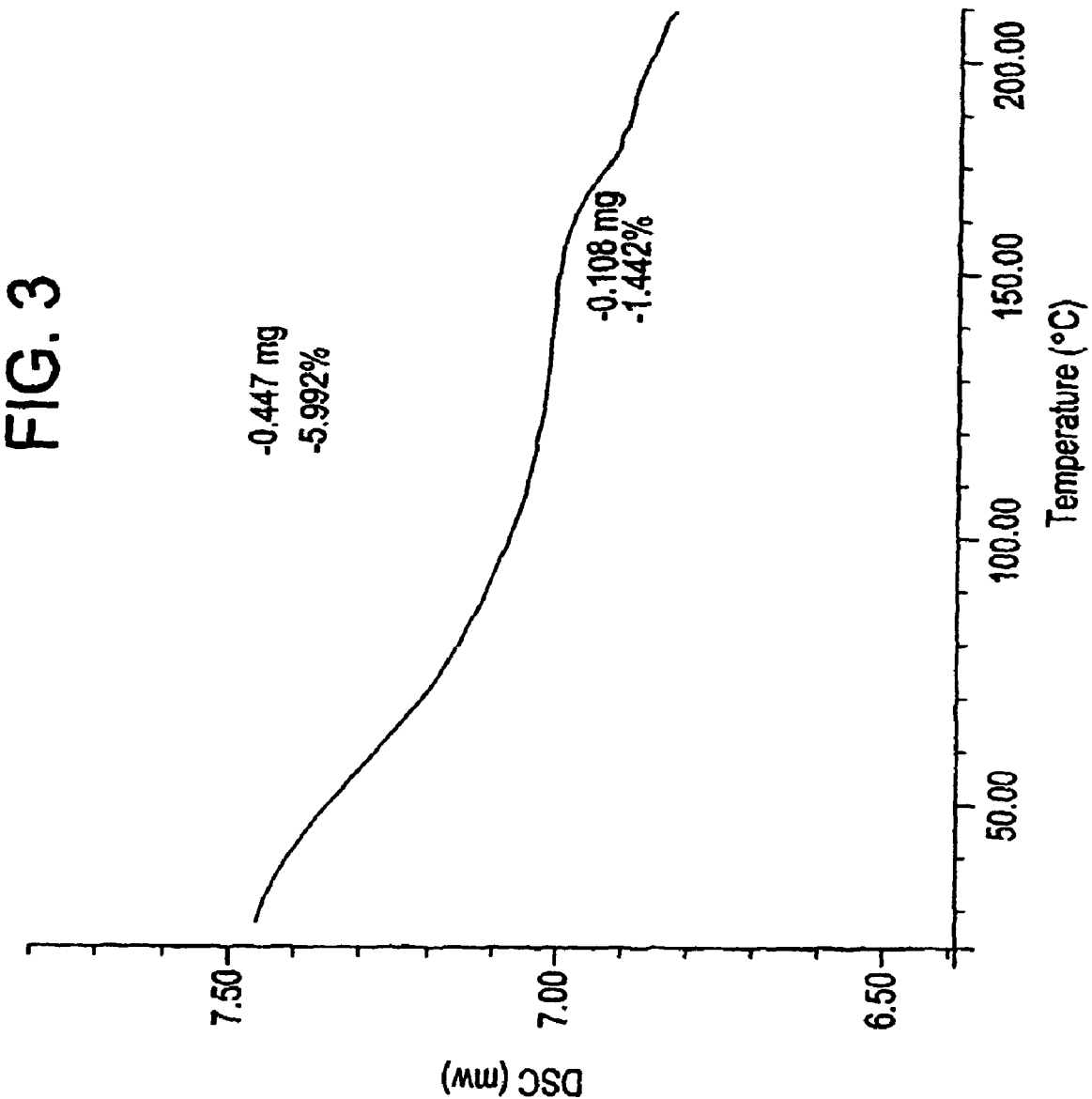

PREPARATION OF AMORPHOUS HYDROUS ESOMEPRAZOLE MAGNESIUM

BACKGROUND OF THE INVENTION

Omeprazole and its therapeutically acceptable alkaline salts are well known inhibitors of gastric acid secretion and anti-ulcer agents. These compounds are sulfoxides and have an asymmetric center at the sulfur atom and, thus, exist as optical isomers or enantiomers. Esomeprazole is the (S)(–) enantiomer of omeprazole.

Omeprazole and its therapeutically acceptable alkaline salts are disclosed in EP 000 5129 and EP 124,495, respectively. U.S. Pat. No. 6,162,816 discloses crystalline Form A and crystalline Form B of esomeprazole and characterizes them by X-ray powder diffraction. U.S. Pat. No. 5,693,818 discloses various salts of omeprazole enantiomers, including esomeprazole magnesium. U.S. Pat. No. 6,369,085 discloses a particular crystalline form of esomeprazole magnesium trihydrate.

A number of drugs have been found to exhibit desirable dissolution characteristics and, in some cases, desirable bioavailability patterns when used in a specific solid form, e.g., as an amorphous or crystalline solid. Therefore, there is a continuing need for new solid forms of esomeprazole and methods of their preparation.

SUMMARY OF THE INVENTION

In one aspect, the invention provides a compound, which is a hydrate in the form of an amorphous solid, having the formula

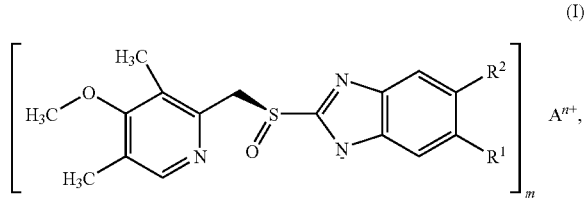

(I)

where one of $R^1$ and $R^2$ is hydrogen and the other is methoxy; A is an alkaline earth or alkali metal; and m and n are 1 or 2. Preferably, the compound of this aspect of the invention is a hydrate of esomeprazole magnesium, which is in the form of an amorphous solid. Various embodiments and variants are provided.

In according with another aspect, the invention provides a composition that includes esomeprazole magnesium as a solid, wherein at least 80% by weight of the solid esomeprazole magnesium is a hydrate of esomeprazole magnesium in the form of an amorphous solid. Various embodiments and variants are provided.

Also part of this invention are processes for making the compounds of the invention, compounds made by these processes, pharmaceutical compositions including any compound of this invention, and methods of treatment of disorders caused by gastric acid secretion, inflammation, infection, or any combination thereof.

BRIEF DESCRIPTION OF THE DRAWINGS

FIG. 3 shows a DSC thermogram for a batch of bulk powder which is a hydrate of esomeprazole magnesium in the form of an amorphous solid.

DETAILED DESCRIPTION OF THE INVENTION

Figure 1:
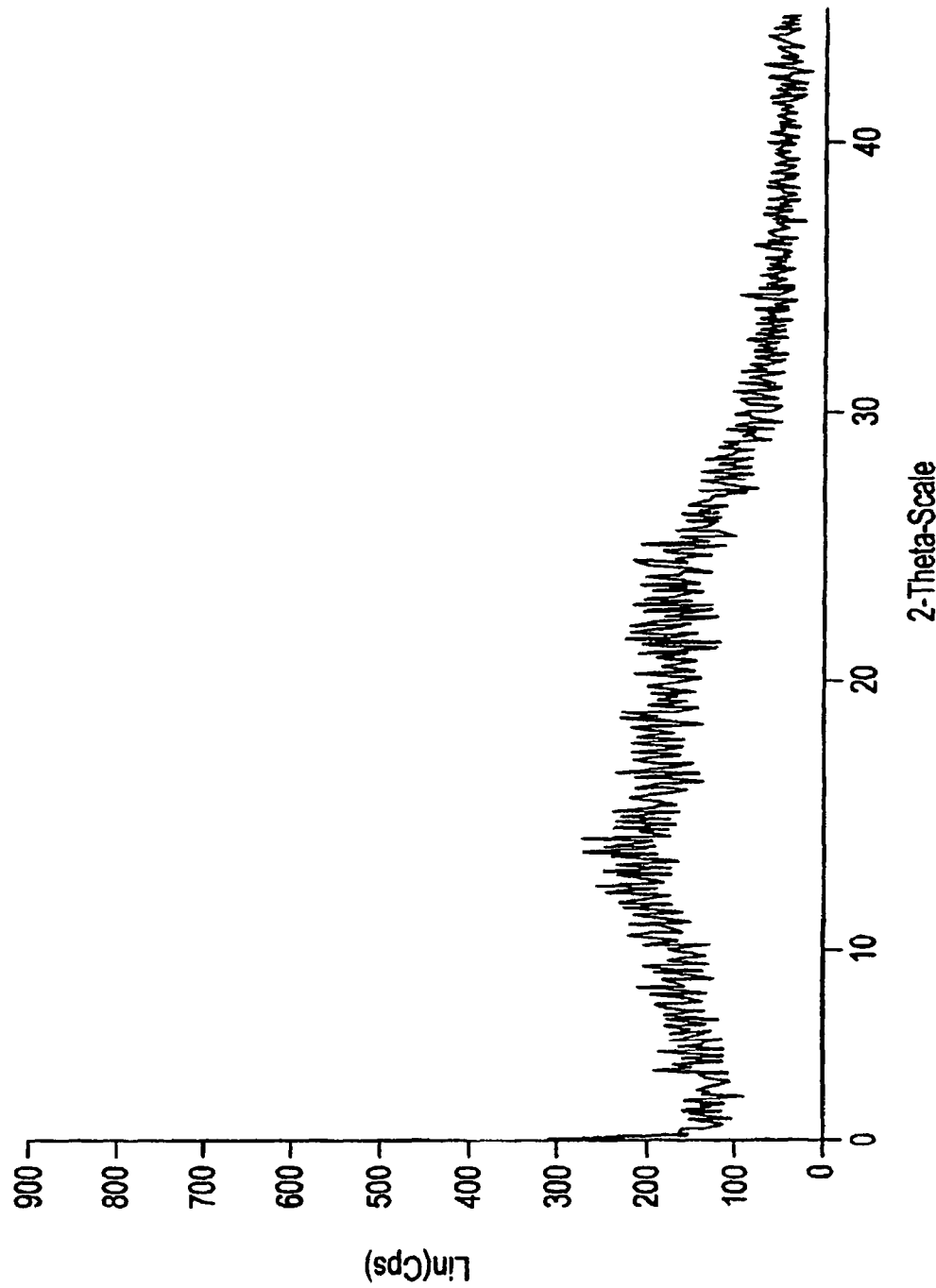
FIG. 1 is an X-ray powder diffractogram for a batch of bulk powder which is a hydrate of esomeprazole magnesium in the form of an amorphous solid.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

Unless stated to the contrary, any use of the words such as "including," "containing," "comprising," "having" and the like, means "including without limitation" and shall not be construed to limit any general statement that it follows to the specific or similar items or matters immediately following it. Except where the context indicates to the contrary, all exemplary values are intended to be fictitious, unrelated to actual entities and are used for purposes of illustration only. Most of the foregoing alternative embodiments are not mutually exclusive, but may be implemented in various combinations. As these and other variations and combinations of the features discussed above can be utilized without departing from the invention as defined by the claims, the foregoing description of the embodiments should be taken by way of illustration rather than by way of limitation of the invention as defined by the appended claims.

For purposes of the present invention, the following terms are defined below.

"Pharmaceutically acceptable" means that which is useful in preparing a pharmaceutical composition that is generally non-toxic and is not biologically undesirable and includes, but is not limited to, that which is customarily utilized for veterinary use and/or human pharmaceutical use.

The term "composition" includes, but is not limited to, a powder, a solution, a suspension, a gel, an ointment, an emulsion and/or mixtures thereof. The term composition is intended to encompass a product containing the specified ingredient(s) in the specified amount(s), as well as any product, which results, directly or indirectly, from combination of the specified ingredients in the specified amounts. A "composition" may contain a single compound or a mixture of compounds. A "compound" is a chemical substance that includes molecules of the same chemical structure.

The term "pharmaceutical composition" is intended to encompass a product comprising the active ingredient(s), pharmaceutically acceptable excipients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing the amorphous solid described herein, additional active ingredient(s), and pharmaceutically acceptable excipients.

The term "excipient" means a component of a pharmaceutical product that is not the active ingredient, such as filler, diluent, carrier, and so on. The excipients that are useful in preparing a pharmaceutical composition are preferably generally safe, non-toxic and neither biologically nor otherwise undesirable, and are acceptable for veterinary use as well as human pharmaceutical use. "A pharmaceutically acceptable excipient" as used in the specification and claims includes both one and more than one such excipient.

"Therapeutically effective amount" means the amount of a compound that, when administered for treating or preventing a disease, is sufficient to effect such treatment or prevention for the disease. The "therapeutically effective amount" will vary depending on the compound, the disease and its severity and the age, weight, etc., of the patient to be treated.

When referring to a chemical reaction, the terms "treating", "contacting" and "reacting" are used interchangeably herein and refer to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "substantially free of" in reference to a composition, as used herein, means that the substance from which the composition is free of cannot be detected by methods known to those skilled in the art.

"About" means the exact number modified by the word, and in addition a reasonable range of values surrounding that number, as would be recognized by a skilled person as forming a reasonable range with regard to the number measured, the property measured, synthesis, detectability, operating parameters of instruments, and other relevant factors.

The term "solvent" may be used to refer to a single solvent or a mixture of solvents. An "alcohol-containing solvent" means a solvent which contains an alcohol. For example, a single alcohol, a mixture of different alcohols, and a mixture of an alcohol with one or more non-alcohol solvents, which non-alcoholic solvents may be organic or aqueous, all qualify as "alcohol-containing solvent(s)". The term "non-aqueous solvent" and the term "organic solvent" may be used interchangeably to mean a solvent conventionally understood as such in the art, including a solvent in which non-polar or hydrophobic compounds are preferentially and substantially soluble. The term "aqueous solvent" preferably means a solvent containing water, or a solvent in which polar or hydrophilic compounds are preferentially and substantially soluble. The term "haloalkane" means an alkane with one or more halogen substituents, which alkane may have one to six carbons, preferably one to three carbons, and be branched or unbranched.

In one aspect, the invention provides a compound having the formula

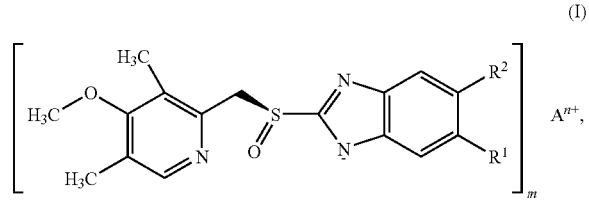

where one of $R^1$ and $R^2$ is hydrogen and the other is methoxy; A is an alkaline earth or alkali metal; and m and n are 1 or 2, the compound being a hydrate and being in the form of an amorphous solid. Examples of A include lithium, sodium, potassium, calcium, and magnesium. m and n should be equal if a neutral salt is desired, if they are not equal the compound will carry a net charge. One salt may be converted to the salt of another cation by conventional methods of exchanging the cation, for example on a cation exchange resin saturated with the desired cation, or by taking advantage of differential solubility of the salts.

In a preferred embodiment, the compound of the formula (I) preferably has m and n that are both 2, and A is magnesium, i.e., the compound is a magnesium salt of esomeprazole. Esomeprazole ((S)(−)$_5$-methoxy-2-[[(4-methoxy-3,5-dimethyl-2-pyridinyl)-methyl]sulphinyl]-1H-benzimidazole; the S(−)enantiomer of omeprazole), as well as its salts, is an active gastric acid secretion inhibitor. Preferably, the hydrate of esomeprazole magnesium is a trihydrate, which contains approximately three water molecules. FIG. 1 shows an X-ray diffractogram of one batch of solid esomeprazole magnesium obtained by the inventors (the process of making the compounds described herein is described in greater details below). An XRD pattern that shows Po significant peaks is characteristic of an amorphous solid. As seen in reference to FIG. 1, the XRD pattern shows no peaks and has a plain halo, demonstrating the amorphous nature of the solid. The x-ray powder diffractogram was measured on a Bruker Axs, D8 Advance X-ray Powder diffractometer with Cu K alpha-1 radiation source.

In another aspect, the invention provides a composition including esomeprazole magnesium as a solid, in which at least 80%, preferably 90%, more preferably 95%, and most preferably 99% by weight of the solid esomeprazole magnesium is a hydrate of esomeprazole magnesium in the form of an amorphous solid. The remainder of the esomeprazole magnesium in the composition, e.g., 20%, preferably 10%, more preferably 5%, and most preferably 1% or less of the total weight of esomeprazole magnesium, may be one or more crystalline forms of esomeprazole magnesium. In one embodiment of this composition, the solid esomeprazole magnesium hydrate is substantially free from crystalline forms of esomeprazole magnesium. In yet another embodiment, in addition to a hydrate of esomeprazole magnesium in the form of an amorphous solid, the composition includes at least a small amount of crystalline forms of esomeprazole magnesium. In a non-limiting example, the composition includes 95% of the hydrate of esomeprazole magnesium in the form of an amorphous solid and at least 1% of any crystalline form of esomeprazole magnesium. In another non-limiting example, the composition includes at least 80% of the hydrate of esomeprazole magnesium in the form of an amorphous solid and at least 5% of other crystalline forms of esomeprazole magnesium. All compositions, in 0.1% increments, which include at least 80% of the hydrate of esomeprazole magnesium in the form of an amorphous solid and at least 1% of crystalline forms of esomeprazole magnesium, are contemplated. All percentages are based upon the total amount of the solid esomeprazole magnesium in the composition.

Figure 2:
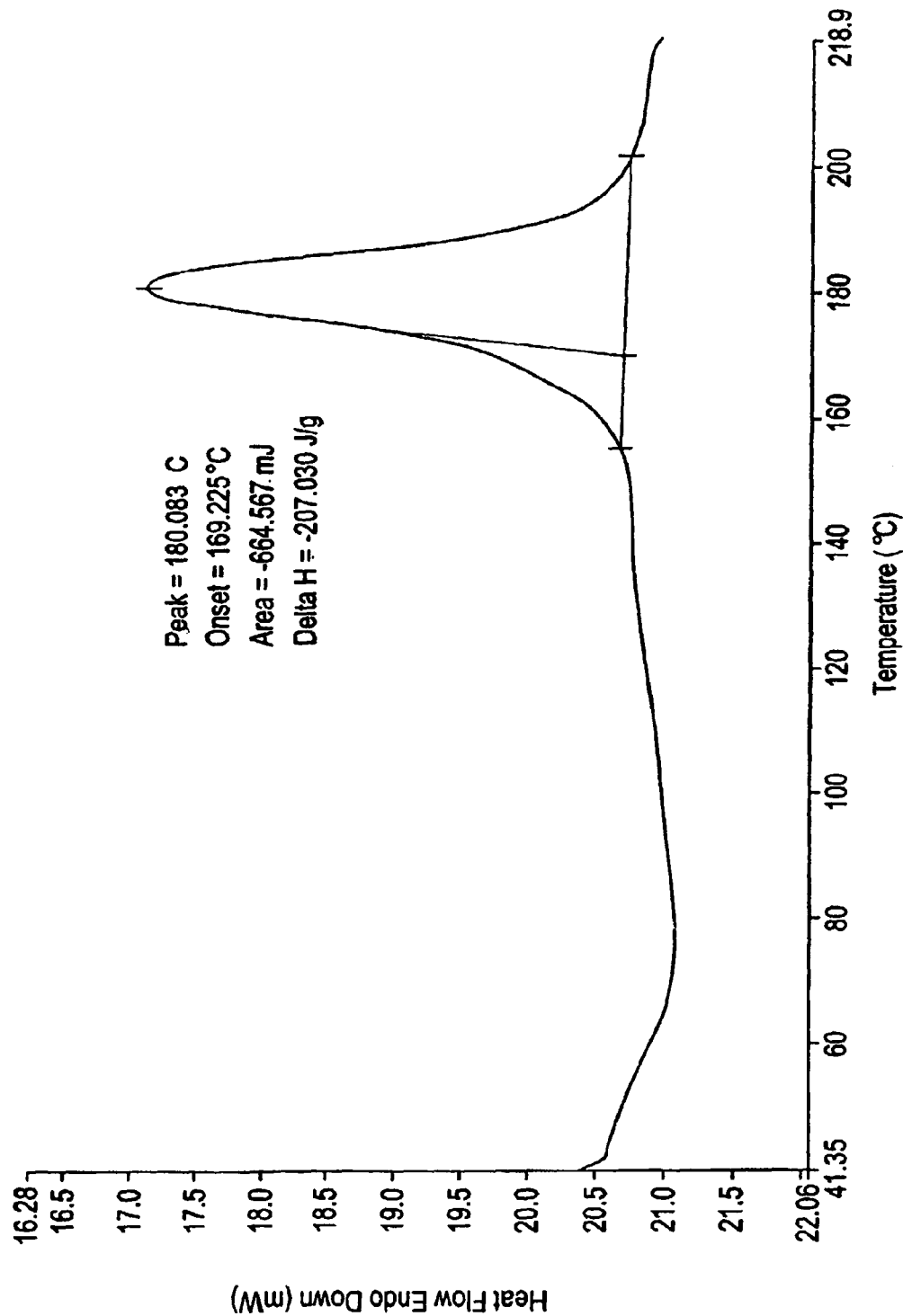
FIG. 2 shows a TGA thermogram for a batch of bulk powder which is a hydrate of esomeprazole magnesium in the form of an amorphous solid.

The preferred form of the composition of this aspect of the invention is a solid powder of bulk esomeprazole magnesium for use as an active pharmaceutical ingredient. This powder composition has a moisture content, which is preferably from about 2% to about 10% as measured by the Karl Fischer method, and more preferably from about 7% to about 8%. Moisture content may be measured by any accepted technology, for example by using Karl Fischer reagent (KF) and an appropriate instrument (goniometer) such as a Mettler DL-35, a Scintag PAD V, a Brukker D5000, or by thermogravimetric analysis using moisture analysis instruments such as the Mettler DSC20, TG50, and TC10A. FIG. 2 shows a TGA thermogram for a batch of bulk powderwhich is a hydrate of esomeprazole magnesium in the form of an amorphous solid. FIG. 3 shows a DSC thermogram for a batch of bulk powder which is a hydrate of esomeprazole magnesium in the form of an amorphous solid.

To determine the relative amounts of amorphous and crystalline components in the composition of this aspect of the invention, one suitable analytical methodology is X-ray powder diffraction (XRD). XRD methodology is capable of providing both qualitative and quantitative information about compounds present in a solid sample. XRD is adaptable to quantitative applications because the intensities of the diffraction peaks of a given compound in a mixture are proportional to the fraction of the material in the mixture. By measuring the intensity of the diffraction lines and comparing them with standards, it is possible to make a quantitative analysis of crystalline mixtures.

As explained above, amorphous solids have no characteristic peaks. In contrast, each crystalline solid is arranged in a set of planes separated by interplanar space d, and exhibits a diffraction pattern with a unique set of peaks generated when x-rays strike a plane at angle theta and are diffracted at the same angle, thus the 2 theta angle is determined by the spacing between a particular set of planes. The identification of a crystalline solid is based upon peaks in the XRD pattern being tabulated in terms the diffraction angle 2 theta (or d-spacing) and their relative intensities. Identification of a crystal form of a compound should be based primarily on observed 2 theta angles with lesser importance being attributed to relative peak intensities. Slight variations in observed 2 theta angles or d-spacing values are expected based on the specific diffractometer employed and the sample preparation technique.

Different quantitative techniques are available. For example, two methods may be used to analyze XRD quantitatively: the Internal Standard Method and the External Standard Method. The Internal Standard Method is the preferred procedure for analyzing powdered systems. This method measures a known quantity of a reference powder which is added to an unknown powder. The mass absorption coefficient of the mixture need not be known in advance. Any number of constituents in the mixture may be quantified independently, including the amorphous (non-crystalline) components. The External Standard Method is used to analyze solid systems when the mass absorption co-efficient is known. It allows the quantification of one or more components in a system, which may contain an amorphous fraction. The percent composition of a crystalline compound can be determined in an unknown composition. The XRD patterns of an unknown composition can be compared to a known standard containing pure crystalline compound to identify the percent ratio of the crystalline form of the compound. This is done by comparing the relative intensities of the peaks from the diffraction pattern of the unknown composition with a calibration curve based on the XRD pattern for the strongest peak derived from the XRD pattern of a pure crystalline sample of the compound. The peak intensities are reported as intensities relative to the peak intensity of the strongest peak ("the 100% peak"). The calibration curve may be created in a manner known to those of skill in the art. For example, five or more artificial mixtures of amorphous and crystalline forms of crystalline compound in different amounts, may be prepared. As an example, such mixtures may contain, 2%, 5%, 7%, 8%, and 10% of crystalline compound, with the remainder being the amorphous form of the salt. Then, XRD patterns are obtained for each artificial mixture using standard XRD techniques. Slight variations in peak positions, if any, may be accounted for by adjusting the location of the peak to be measured. The intensities of the 100% peak(s) for each of the artificial mixtures are then plotted against the known weight percentages of the crystalline form. The resulting plot is a calibration curve that allows determination of the amount of crystalline compound in an unknown sample. For the unknown mixture of crystalline and amorphous compounds, the intensities of the 100% peak(s) in the mixture, relative to an intensity of this peak in a calibration mixture, may be used to determine the percentage of the crystalline form in the composition, with the remainder determined to be the amorphous material.

In order to determine the relative amount of amorphous to crystalline solid in compositions of this invention, XRD information may be used to create the calibration curve(s) described above. For use in this comparative analysis, XRD patterns of crystalline forms of esomeprazole are obtainable by known methods of measurement. In addition, the XRD data for crystalline Form I esomeprazole magnesium trihydrate is disclosed in U.S. Pat. No. 6,369,085, which is incorporated by reference for this purpose. The XRD data for crystalline form II esomeprazole magnesium trihydrate were obtained by the inventors:

| 2-theta value | Relative Intensity (%) |
|---|---|
| 4.824 | 100.0 |
| 18.471 | 81.7 |
| 5.552 | 43 |
| 14.16 | 28.1 |
| 12.104 | 25.3 |
| 8.608 | 22.3 |
| 21.089 | 21.5 |
| 7.411 | 18.8 |

In another aspect, the invention provides a process for making a hydrate of esomeprazole magnesium in the form of an amorphous solid by a) providing esomeprazole magnesium in an alcohol-containing solvent, b) contacting the esomeprazole magnesium in the alcohol-containing solvent with water so that a solid mass separates, and c) isolating the separated solid mass (for example by filtration), which is the hydrate of esomeprazole magnesium in the form of an amorphous solid. The starting materials and reagents used in this process are commercially available and/or may be readily synthesized by a skilled person, unless otherwise indicated. Esomeprazole base may be made as described in the Reference Example below from omeprazole sodium, the preparation of which is well known in the art. See in addition U.S. Pat. Nos. 6,162,816 and 5,693,818, which are incorporated herein by reference.

Any conventional aqueous or organic solvent that would not hinder or would contribute to the reactions by which the process of the invention proceeds may be included in the alcohol-containing solvent. Examples of organic solvents include chlorinated alkanes, such as chloroform, dichloromethane, dichloroethane and carbon tetrachloride; ketones (including alkyl ketones), such as acetone, ethyl methyl ketone, methyl isobutyl ketone, and diethyl ketone; ester solvents such as lower alkyl esters of organic acids, such as methyl, ethyl, propyl isopropyl, butyl, isobutyl, and tert-butyl acetate; and nitriles, such as acetonitrile. The alcohol component of the alcohol-containing solvent is preferably methanol, ethanol, propanol, or butanol, more preferably ethanol, n-propanol, tert-butanol, n-butanol, and most preferably methanol. The alcohol-containing solvent may be a pure alcohol (for example, methanol) or may be a mixture of alcohol with other solvent(s), for example with water, with a ketone solvent such as acetone, or with both. Preferably the alcohol-containing solvent includes methanol.

Certain operational steps are well known in the art and, unless otherwise indicated, any known method for performing these functions may be used in the processes of this invention. For example, solvents may be removed by distillation in atmosphere or under vacuum. Drying may be accomplished by evaporation, spray drying, drying under vacuum, and freeze-drying. Stirring means any method for blending or mixing a reaction mixture. Reagents and/or reaction mixtures may be combined by adding one to the other, for example, water may be poured into a reaction mixture. In general the methods of this invention involve various such steps, e.g. combining esomeprazole base with a suitable counterion such as magnesium, to form esomeprazole magnesium, hydrating the esomeprazole magnesium by combining with water to form an esomeprazole magnesium hydrate, removing organic impurities and excess magnesium, and drying the esomeprazole magnesium hydrate (preferably trihydrate) to obtain a hydrate of esomeprazole magnesium in the form of an amorphous solid.

In one embodiment of this aspect of the invention, esomeprazole magnesium is provided by suspending magnesium metal in an alcohol-containing solvent in the presence of a haloalkane and adding esomeprazole base (which may itself be dissolved in an alcohol-containing solvent). Preferred haloalkanes are dichloromethane, dichloromethane (in particular 1,2-dichloroethane) and trichloromethane (chloroform); most preferably, dichloromethane. The process then continues by contacting with water as described above. Contacting with water may be accomplished by pouring water into the esomeprazole magnesium solution, or by pouring the esomeprazole magnesium solution into water, or by other conventional methods. The preferred amounts of alcohol-containing solvent and of water in milliliters (ml) may be determined relative to the amount of the starting esomeprazole magnesium (i.e., the esomeprazole magnesium in the alcohol-containing solvent provided in the first step of the process) in grams (g). The amount of alcohol-containing solvent is preferably about 5 ml to about 10 ml per 1 gram of the starting esomeprazole magnesium, preferably about 6 to about 7 ml. The amount of water is preferably about 5 ml to about 25 ml per 1 gram of the starting esomeprazole magnesium, preferably about 18 ml.

After the solid mass is isolated, it is helpful to wash it in a suitable solvent, such as water or a ketone solvent such as acetone, preferably once with water and once with acetone. However the solid mass may be washed sequentially in these solvents in any combination, for example twice with water and once with the ketone solvent, or the reverse, and so on. It is also helpful to dissolve the isolated solid mass (preferably after filtration, or after filtration and washing) in an alcohol such as methanol. At this stage the solution formed by dissolving the solid mass in the alcohol may be filtered to separate the excess magnesium, which may then be removed by conventional methods. The solution formed by dissolving the isolated solid mass in alcohol is treated to obtain solid material again in the form of an isolated mass. Solvent may be removed from the solution to accomplish this, using conventional methods. The isolated residual mass is preferably reprecipitated, for example from an ester solvent such as ethyl acetate.

In another embodiment of this aspect of the invention, the esomeprazole magnesium is provided in methanol or a mixture of methanol with acetone and water, preferably in an amount of about 5 ml to about 10 ml per 1 gram of the starting esomeprazole magnesium. The esomeprazole magnesium provided in methanol or a mixture of methanol with acetone and water is then concentrated to about 80% of its original volume, reducing the ratio of the solvent (the methanol or the mixture of methanol with acetone and water) to the starting esomeprazole magnesium. After the concentrated solution of the esomeprazole magnesium in the alcohol-containing solvent is contacted with water so that a solid mass separates, it is helpful to filter the solid mass and wash it with water. It is possible to seed esomeprazole magnesium in the alcohol-containing solvent (for example methanol or a mixture of methanol with acetone and water) with esomeprazole magnesium in the form of an amorphous solid, for example by adding the latter to the water with which the former is contacted.

One specific variant of this aspect of the invention involves dissolving magnesium at a temperature of 30° C. to 60° C. in a straight or branched lower alkanol (one to four carbons) solvent, adding haloalkane (one to three carbons) solvent, cooling to 0° C. to 15° C., adding esomeprazole base in a straight or branched lower alkanol solvent to generate a reaction mass, decomposing the reaction mass by pouring the mass into water and stirring for one to two hours, filtering out the resulting solid by conventional methods, suspending the solid obtained by filtering in a solvent such as acetone and stirring for one to two hours, filtering out the solid from the suspension by conventional methods (to remove excess magnesium), dissolving the solid resulting from the filtering in a straight or branched lower alkanol solvent and filtering the solution a straight or branched lower alkanol solvent, distilling off the solvent from the filtrate under reduced pressure, suspending the resulting solid in a solvent such as ethyl acetate (to crystallize solid), then either filtering by conventional methods; or adding esomeprazole magnesium in the form of an amorphous solid as seeding material and cooling to a temperature of 0° C. to 20° C. and then filtering by conventional methods, and drying the resulting solid at a temperature of 30° C. to 100° C., preferably 60° C., to obtain a hydrate of esomeprazole magnesium in the form of an amorphous solid.

In another aspect, the invention provides part pharmaceutical compositions which include a hydrate of esomeprazole magnesium in the form of an amorphous solid. Pharmaceutical compositions generally contain, in addition to the active compound or compounds, one or more carriers (also called excipients) which ordinarily lack pharmaceutical activity per se, but have various useful properties which can, for example, enhance the stability, sterility, bioavailability, and ease of formulation of a pharmaceutical composition. These carriers are pharmaceutically acceptable, meaning that they are not harmful to humans or animals when taken appropriately and are compatible with the other ingredients in a given formulation. The carrier may be solid, semi-solid, or liquid, and may be formulated with the compound in bulk, but ultimately in the form of a unit-dose formulation (i.e., a physically discrete unit containing a specific amount of active ingredient) such as a tablet or capsule.

The pharmaceutical compositions of this invention are contemplated in various formulations suitable for various modes of administration, including but not limited to inhalation, oral, rectal, parenteral (including subcutaneous, intradermal, intramuscular, intravenous), implantable, intravaginal and transdermal administration. The most suitable route of administration in any given case depends on the duration of the subject's condition, the length of treatment desired, the nature and severity of the condition being treated, and the particular formulation that is being used. The formulations may be in bulk or in unit dosage form, and may be prepared by methods well known in the art for a given formulation.

The amount of active ingredient included in a unit dosage form depends on the type of formulation in which the active ingredient is presented. A pharmaceutical composition will generally contain about 0.1% by weight to about 99% by weight of active ingredient, preferably about 1% by weight to 50% by weight for oral administration and about 0.2% by weight to about 20% by weight for parenteral administration.

Formulations suitable for oral administration include capsules (hard and soft), cachets, lozenges, syrups, suppositories, and tablets, each containing a pre-determined amount of the active compound; as a powder or granules; as a solution or a suspension in an aqueous or non-aqueous liquid; or as an oil-in-water or water-in-oil emulsion. Such formulations may be prepared by any suitable method of pharmacy that includes the step of bringing into association the active compound and a suitable carrier or carriers. The amount of active ingredient per unit dosage of solid formulations is preferably from about 5 mg to 60 mg, in particular about 8 to 10 mg, about 16 to 20 mg, and about 32 to 40 mg. For liquid oral formulations, a preferable amount is from about 2% by weight to about 20% by weight. Suitable carriers include but are not limited to fillers, binders, lubricants, inert diluents, surface active/dispersing agents, flavorants, antioxidants, bulking and granulating agents, adsorbants, preservatives, emulsifiers, suspending and wetting agents, glidants, disintegrants, buffers and pH-adjusting agents, and colorants. Examples of carriers include celluloses, modified celluloses, cyclodextrins, starches, oils, polyols, sugar alcohols and sugars, and others. For liquid formulations sugar, sugar alcohols, ethanol, water, glycerol, and poyalkylene glycols are particularly suitable, and may also be used in solid formulations. Cyclodextrins may be particularly useful for increasing bioavailability. Formulations for oral administration may optionally include enteric coatings known in the art to prevent degradation of the formulation in the stomach and provide release of the drug in the small intestine. Examples of suitable controlled release formulation vehicles are disclosed in U.S. Pat. Nos. 3,845,770; 3,916,899; 3,536,809; 3,598,123; and 4,008,719, the disclosures of which are hereby incorporated by reference in their entirety.

Formulations suitable for buccal or sub-lingual administration include lozenges comprising the active compound in a flavored base, usually sucrose and acacia or tragacanth, although other agents are also suitable, and pastilles comprising the compound in an inert base such as gelatin and glycerin or sucrose and acacia.

Formulations of the present invention suitable for parenteral administration comprise sterile aqueous and non-aqueous injection solutions of the active compound, preferably isotonic with the blood of the intended recipient. The amount of active ingredient is preferably a concentration of from about 0.1% by weight to 10% by weight. These preparations may contain, among other ingredients, anti-oxidants, buffers, bacteriostats, and solutes that render the formulation isotonic with the blood of the intended recipient. Aqueous and non-aqueous sterile suspensions may include, among others, suspending and thickening agents. The formulations may be presented in unit-dose or multi-dose containers, e.g. sealed capsules and vials, and may be stored in a freeze-dried or lyophilized condition requiring only the addition of the sterile liquid carrier, for example, saline or water-for-injection immediately prior to use. Extemporaneous injection solutions and suspensions may be prepared from sterile powders, granules and tablets of the kind previously described.

Formulations suitable for rectal administration are preferably presented as unit dose suppositories. These may be prepared by admixing the active compound with one or more conventional solid carriers, e.g. cocoa butter, and then shaping the resulting mixture.

Formulations suitable for transdermal delivery include ointments, creams, lotions, and oils and contain well known pharmaceutically and cosmetically suitable ingredients. Bases for such formulations include for example alcohols, lanolin, petrolatum, paraffin, polyethylene glycol, emulsifiers, penetration enhancing agents, and oleaginous vehicles such as oils. Skin patches may also be used, typically consisting of a fabric or paper base impregnated with a suitable dose in a transdermal formulation. Formulations suitable for transdermal administration may also be delivered by iontophoresis, and typically take the form of an optionally buffered aqueous solution of the active compound.

Also part of this invention are methods of treatment using one or more of the compounds of this invention and the pharmaceutical compositions of this invention. In particular, a hydrate of esomeprazole magnesium in the form of an amorphous solid may be administered to a subject in an amount effective to reduce secretion of gastric acid by that subject. Although it is possible to use compounds and compositions of this invention to prevent secretion of gastric acid by establishing a dosage level effective to do so, such treatment would only be applicable in special cases, since to alleviate or eliminate most of the conditions discussed above which are treated with the compounds of this invention, gastric acid secretion should not be eliminated altogether, but only reduced in amount or duration. In general, the treatment may be determined to alleviate, to eliminate, or to prevent a given condition based on factors determinable by a skilled physician as discussed below in the context of determining an effective amount for dosage. Further, the compounds of this invention may be administered to a subject for treating a disorder caused by gastric acid secretion by administering to a subject an amount effective to reduce gastric acid secretion by said subject.

The compounds and compositions of this invention may be used for treatment of any specific disorder or condition related to other conditions known to be suitable for treatment by omeprazole compounds. These compounds and compositions are useful for ameliorating or preventing conditions related to secretion of gastric acid, such as ulcers (including those caused by *H. pylori*), heartburn, gastro-esophageal reflux, esophagitis, hypersecretory conditions (e.g. Zollinger-Ellison, endocrine adenoma, systemic mastocytosis), gastritis, duodenitis, dyspepsia, acute gastrointestinal bleeding (especially upper), for patients on NSAID therapy or in intensive care, to reduce or prevent gastric acid aspiration and stress ulceration. These compounds are also useful for treating inflammatory conditions such as psoriasis and lysosomal enzyme problems, and infections such as those caused by *H. pylori*.

By subject is meant a human or an animal, preferably human. Animals contemplated by this invention include any animal safely treatable by compounds of this invention, preferably mammals such as bovines, ovines, caprines, equines, felines, canines, rodents, leporids, and other mammalian farm and zoo animals or domestic pets. The effective amount (i.e. dosage) of active compound for treatment will vary depending on the route of administration, the condition being treated, its severity, and duration, and the state and age of the subject. A skilled physician will monitor the progress of the subject and will adjust the dosage accordingly, depending on whether the goal is to eliminate, alleviate, or prevent a given condition.

Generally, the starting dosage may be low, but must at least start from the low end of the effective range, and in cases of severe ulcers it may be increased, and the active substance may be administered as maintenance therapy. The dosage of the active compound may be towards the high end of the effective range, or if needed even higher, but should be considered in proportion to the subject's weight. Depending on the solubility of the particular formulation of active compound administered, the daily dose may be divided among one or several unit dose administrations. Administration of the active compounds may be carried out therapeutically, i.e. as a rescue treatment, or prophylactically, and may be maintained for prolonged periods of time. One skilled in the art will take such factors into account when determining dosage. In general oral and parenteral dosages will be in the range of about 5 to about 350 to 400 mg per day of active ingredient, preferably about 8 mg to about 60 mg, most preferably about 10 mg to about 40 mg.

Unless stated to the contrary, words and phrases such as "including," "containing," "comprising," "having", "for example", "i.e.", "in particular" and the like, mean "including without limitation" and shall not be construed to limit any general statement that it follows to the specific or similar items or matters immediately following it. Any values presented as exemplary values are intended to be used for purposes of illustration. Most of the foregoing alternative embodiments are not mutually exclusive, but may be implemented in various combinations. As these and other variations and combinations of the features discussed above can be utilized without departing from the invention as defined by the claims, the foregoing description of the embodiments should be taken by way of illustration rather than by way of limitation of the invention as defined by the appended claims.

The Examples provided below are illustrative and are not intended to limit the scope of the claimed invention.

REFERENCE EXAMPLE

Preparation of Esomeprazole Base

Omeprazole sodium (500 grams) was suspended in acetone (6.0 liters) and diethyl D-tartrate (280 grams), titanium (IV) isopropoxide (325 grams) and triethylamine (410 grams) were added sequentially at a temperature of 35-40° C. L (+) mandelic acid (207 grams) was then added and further stirred for 30-60 minutes. The separated solid was filtered, washed with acetone (500 ml) and suck dried under vacuum. The wet solid thus resulting was suspended in a mixture of dichloromethane (2.0 liters) and 5% sodium bicarbonate solution (2.0 liters) and stirred for 15-30 minutes. The dichloromethane layer was separated from the resulting solution and the solvent was distilled off up to substantial completion to get the title compound in residual mass. [Weight: 180 grams, Chiral Purity: 99.93% (S-Isomer)].

Example 1

Magnesium metal (1.55 grams) was suspended in methanol (111 ml), dichloromethane (3.7 ml) was added, and stirred for 1-2 hours at a temperature of 50-60° C. The mass was cooled to a temperature of 5-10° C. and esomeprazole base (37.0 grams, prepared as per reference example) and methanol (111.0 ml) were added accompanied by stirring for 15-30 minutes. The reaction mass was decomposed by pouring into water (666 ml) at a temperature of 5-10° C. over a period of 45-60 minutes. The reaction mass was further stirred for 30-45 minutes to separate the solid mass. The solid mass was filtered, washed with water (222 ml) and suck dried under vacuum. The wet solid was suspended in acetone (148 ml) and stirred for 15-30 minutes at a temperature of 5-10° C. The solid mass was filtered and washed with acetone (37 ml). The compound obtained was dissolved in methanol (222 ml) and the solution filtered to separate the excess magnesium. The solvent was distilled off from the distillate at a temperature of 35-40° C. under reduced pressure to get the residual mass.

The residual mass was crystallized in ethyl acetate (100 ml) at a temperature of 25-35° C. and stirred for 10-15 minutes. The crystallized mass was further stirred at a temperature of 0-5° C. for 1-2 hours. The crystallized solid was filtered, washed with ethyl acetate (50 ml) and dried at 60-65° C. to afford a hydrate of esomeprazole magnesium in the form of an amorphous solid.

[Weight: 10.0 grams, Chiral Purity: 99.4%, Optical rotation: −125.8° (c=0.5% methanol) and M.C. by KF: 6.16%]. KF was measured on Mettler DL-35 instrument using Karl Fischer reagent.

Example 2

Esomeprazole magnesium in methanol solution (660 ml, which is equivalent to 100 grams of esomeprazole base, prepared as per Example 1) and acetone (30 ml) and water (30 ml) were stirred for 10-15 minutes at room temperature. Then the reaction mixture was allowed to settle and the unwanted material was filtered off. The filtrate was distilled to 80% of its initial volume. The concentrated reaction mass was poured slowly in to water (750 ml) under stirring. The resulting reaction mass was cooled to a temperature of 0-5° C. and stirred to isolate the solid. Then the isolated solid was filtered, washed with water (300 ml) and dried at a temperature of 60-70° C. to yield a hydrate of esomeprazole magnesium in the form of an amorphous solid. KF was measured on Mettler DL-35 instrument using Karl Fischer reagent.

[Weight: 30.0 grams, M.C. by KF: 7.0%].

Example 3

A methanolic solution of esomeprazole magnesium (660 ml, which is equivalent to 100 grams of esomeprazole base, prepared as per Example 1) was concentrated to 80% of its initial volume under reduced pressure. The concentrated reaction mass was poured slowly in to water (750 ml) containing the amorphous form of esomeprazole magnesium (0.1 gram) as seeding material at a temperature of 0-5° C. The resulting reaction mass was stirred to isolate the solid. Then the isolated solid was filtered, washed with water (300 ml) and dried at a temperature of 60-70° C. to yield a hydrate of esomeprazole magnesium in the form of an amorphous solid. KF was measured on Mettler DL-35 instrument using Karl Fischer reagent.

[Weight: 30.0 grams, M.C. by KF: 7.2%].

Example 4

A methanolic solution of esomeprazole magnesium (100 ml, which is equivalent to 60 grams of esomeprazole base, prepared as per Example 1) was concentrated to 80% of its initial volume under reduced pressure. The concentrated reaction mass was poured slowly in to ethyl acetate (500 ml) containing amorphous form of esomeprazole magnesium (0.1 gram) as seeding material at a temperature of 0-5° C. The resulting reaction mass was stirred to isolate the solid. Then the isolated solid was filtered, washed with ethyl acetate (100 ml) and dried at a temperature of 60-70° C. to yield a hydrate of esomeprazole magnesium in the form of an amorphous solid. KF was measured on Mettler DL-35 instrument using Karl Fischer reagent.

[Weight: 21.0 grams, M.C. by KF: 8.7%].

The invention claimed is:

1. Amorphous esomeprazole magnesium having a moisture content of about 6.2 percent.

2. Amorphous esomeprazole magnesium having a moisture content of about 7 percent.

3. Amorphous esomeprazole magnesium having a moisture content of about 7.2 percent.

4. Amorphous esomeprazole magnesium having a moisture content of about 8.7 percent.

5. Amorphous esomeprazole magnesium having a moisture content from about 7 percent to about 8 percent.

* * * * *